United States Patent
Wang et al.

(10) Patent No.: US 7,345,138 B2
(45) Date of Patent: *Mar. 18, 2008

(54) BIODEGRADABLE POLYPHOSPHATES FOR CONTROLLED RELEASE OF BIOACTIVE SUBSTANCES

(75) Inventors: Jun Wang, Baltimore, MD (US); Hai-Quan Mao, Singapore (SG); Kam Weng Leong, Ellicott City, MD (US)

(73) Assignee: Johns Hopkins Singapore PTE Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 10/499,898

(22) PCT Filed: May 14, 2002

(86) PCT No.: PCT/SG02/00090

§ 371 (c)(1),
(2), (4) Date: Feb. 14, 2005

(87) PCT Pub. No.: WO02/092667

PCT Pub. Date: Nov. 21, 2002

(65) Prior Publication Data

US 2005/0131200 A1 Jun. 16, 2005

Related U.S. Application Data

(60) Provisional application No. 60/290,888, filed on May 14, 2001.

(51) Int. Cl.
*C08G 63/68* (2006.01)
*C08G 79/02* (2006.01)

(52) U.S. Cl. .................................... 528/287; 528/398
(58) Field of Classification Search ................ 528/287, 528/398
See application file for complete search history.

(56) References Cited

U.S. PATENT DOCUMENTS 6,852,709 B2 * 2/2005 Leong et al. .................. 514/75

FOREIGN PATENT DOCUMENTS

WO     WO 8301778     * 5/1983

OTHER PUBLICATIONS

CA 123:144517 "Amino acids coupled to poly(alkylene phosphates", Penczek et al.*

* cited by examiner

*Primary Examiner*—Nathan M. Nutter
(74) *Attorney, Agent, or Firm*—Marlan D. Walker; Peter J. Gluck; Greenberg Traurig

(57) ABSTRACT

The present invention is directed to a biodegradable system for the controlled release of bioactive substances. This system comprises novel biodegradable and biocompatible polyphosphoesters that carry positive charges. Process for making these polyphosphoesters, compositions containing these polyphosphoesters and biologically active substances, articles and methods for delivery of drugs and genes using this system are described. A controlled gene delivery system based on these polyphosphoesters is prepared by complex coacervation of nucleic acid (DNA or RNA) with polymers. The release rates can be manipulated by adjusting the charge ratios of polyphosphoesters to nucleic acids. This gene delivery system yields a higher gene expression in muscle when injected intramuscularly.

5 Claims, 4 Drawing Sheets

BIODEGRADABLE POLYPHOSPHATES FOR CONTROLLED RELEASE OF BIOACTIVE SUBSTANCES

This application claims the benefit of U.S. Provisional Application Ser. No. 60/290,888 filed May 14, 2001, the teachings of which are incorporated herein by reference.

BACKGROUND OF THE INVENTION

1. Field of the Invention

The present invention generally relates to biodegradable polymer compositions, in particular those containing both phosphoester linkages in the polymer backbone and chargeable groups linked to the backbone through a phosphoester bond. These biodegradable polymers of the invention are designed for the controlled release of drugs and genes, particularly as carriers for gene therapy and for the delivery of protein drugs. The invention also has wide applicability in tissue engineering applications, where the sustained delivery of growth factors is achieved through gene transfer.

2. Background

Polymeric controlled drug delivery has significantly improved the success of many drug therapies (Langer, 1990, *New methods of drug delivery, Science* 249: 1527-33; Poznansky, et al., 1984, *Biological approaches to the controlled delivery of drugs: a critical review, Pharmacol. Rev.* 36: 277-336). In such a delivery system, pharmacokinetics and biodistribution of the drug depend upon the physiochemical properties and/or degradation properties of the polymer carriers. In general, polymeric carriers offer advantages over other delivery systems: polymeric systems potentially have more controllable release kinetics, better stability in storage, and have better biocompatibility. A biodegradable drug-carrier could offer features difficult to attain from non-biodegradable systems. Other than obviating the need to remove the drug-depleted devices, a biodegradable system is also applicable to a wider range of drugs. More and more new polymer carriers have been proposed for controlled drug delivery, although poly(lactide-co-glycolide) copolymers still dominate the field. There is clearly justification to continue to develop new biodegradable drug-carriers, because of the increasing need in the emerging new applications. The widening scope of applications requires polymeric carriers to assume different configurations and serve additional functions other than just passive delivery. For instance, applying the controlled release device as more than just a monolithic matrix, for example, as a coating material for a drug-eluting stent, may obligate the polymer to have elastomeric properties. In the new and exciting field of tissue engineering where local and sustained delivery of growth factors and/or genes encoding these growth factors may influence the course of tissue development, the drug-carrier may also need to perform a double-duty to provide structural support or scaffolding functions. To achieve active targeting, it would involve conjugation of ligands to the polymeric carriers, which requires the polymeric carrier to contain functional groups for derivatization. In the field of gene delivery, polymeric gene carriers need to be of polycationic nature and should have the structural flexibility to include targeting feature and parameters affecting the intracellular trafficking of the genes (Han, et al., 2000, *Development of biomaterials for gene therapy, Molecular Therapy* 2: 302-317; Varga, et al., 2000, *Receptor-mediated targeting of gene delivery vectors: insights from molecular mechanisms for improved vehicle design. Biotechnol. Bioeng.* 70: 593-605). With such a broad utility for these biodegradable drug-carriers, no one single material can be expected to satisfy all requirements of different applications.

Gene therapy has been progressively developed with the hope that it will be an integral part of medical modalities in the future. Gene delivery system is one of the key components in gene medicine, which directs the gene expression plasmids to the specific locations within the body. The control of gene expression is achieved by influencing the distribution and stability of plasmids in vivo and the access of the plasmids to the target cells, and affecting the intracellular trafficking steps of the plasmids (Mahato, et al., 1999, *Pharmaceutical perspectives of nonviral gene therapy, Adv. Genet.* 41: 95-156). Recently, there is an increasing interest in developing systems for sustained release of DNA. Such a system could be used to achieve localized and enhanced gene expression in skeletal muscle. It would find wide applications in treating muscle and nerve disorders, providing systemic circulation of secretory proteins, and as a genetic vaccine carrier. Encapsulation of DNA in PLGA nanoparticles (Cohen, et al., 2000, *Sustained delivery and expression of DNA encapsulated in polymeric nanoparticles. Gene Therapy* 7: 1896-1905) and absorption of plasmid to the surface of cationic PLGA microparticles (Singh, et al., 2000, *Characterization of cationic microparticles with adsorbed plasmid DNA. Proceed. Int'l. Symp. Control. Rel. Bioact. Mater.*, 27, 6405-6406) have been reported recently to achieve sustained release of plasmid DNA. Sustained release of DNA was observed for 2 to 4 weeks in these systems. The cationic microparticles induced about fourfold higher gene expression level in muscle at day 14, and induced higher Th1 and Th2 responses in mice (Singh, et al., 2000, *Cationic microparticles: A potent delivery system for DNA vaccines. Proc. Natl. Acad. Sci. USA* 97(2): 811-816). However, both systems are limited by the low DNA loading levels (<1%) and the little room for optimization of DNA release kinetics. Other systems currently under investigations are non-biodegradable polymeric systems, e.g. poly (ethylene-co-vinyl acetate) (Luo, et al., 1999, *Controlled DNA delivery systems. Pharm. Res.* 16(8): 1300-1308) and Poloxamers (Lemieux, et al., 2000, *A combination of poloxamers increases gene expression of plasmid DNA in skeletal muscle. Gene Therapy* 7: 986-991). The present patent features a novel gene delivery system that based on the biodegradation of polymeric carriers to achieve a sustained release of plasmid DNA in a controlled manner.

SUMMARY OF THE INVENTION

The invention provides positively chargeable biodegradable polymers that comprises at least one phosphoester linkage in the polymer backbone and at least one positively chargeable group wherein the positively chargeable group is a substitutent of a side chain attached to the polymer backbone through a phosphoester linkage.

The invention further provides positively chargeable biodegradable polymer compositions comprising:

(a) at least one biologically active substance; and (b) A positively chargeable biodegradable polymer comprising at least one phosphoester linkage in the polymer backbone and at least one positively chargeable group wherein the positively chargeable group is a substituent of a side chain attached to the polymer backbone through a phosphoester linkage.

The invention additionally provides a method of preparing a positively chargeable biodegradable polymers. The method comprising the steps of:

polymerizing at least one monomer to form a polymer with at least one phosphoester linkage in the polymer backbone;

reacting the polymer with an alcohol having a positively chargeable group or a substituent that can be functionalized to a positively chargeable group under conditions conducive to the formation of a positively chargeable biodegradable polymer comprising at least one phosphoester linkage in the polymer backbone and at least one positively chargeable group wherein the positively chargeable group is a substitutent of a side chain attached to the polymer backbone through a phosphoester linkage.

The invention provides a method of preparing a positively chargeable biodegradable polymer composition. The method comprises the steps of:

providing a positively chargeable biodegradable polymer comprising at least one phosphoester linkage in the polymer backbone and at least one positively chargeable group wherein the positively chargeable group is a substituent of a side chain attached to the polymer backbone through a phosphoester linkage.

contacting the positively chargeable biodegradable polymer with a biologically active substance under conditions conducive to the formation of a complex comprising the positively chargeable biodegradable polymer and the biologically active substance.

The invention also provides for the controlled release of a biologically active substance in-vivo or in-vitro. The method comprises the steps of:

providing a positively chargeable biodegradable polymer composition comprising:

(a) at least one biologically active substance; and (b) A positively chargeable biodegradable polymer comprising at least one phosphoester linkage in the polymer backbone and at least one positively chargeable group wherein the positively chargeable group is a substituent of a side chain attached to the polymer backbone through a phosphoester linkage;

contacting the composition in vivo or in vitro with a biological fluid, cell or tissue under conditions conducive to the delivery of at least a portion of the biologically active substance to the biological fluid, cell or tissue.

The invention further provides methods for gene transfection using the controlled release methods and the positively chargeable biodegradable polymer composition comprising a DNA sequence, a gene or a gene fragment, to deliver a DNA sequence, a gene or a gene fragment to a specified tissue target in a patient. Gene transfection methods of the invention are suitable for use in treatment of any disease or disorder which is currently treatable by gene therapy or is contemplated as a disease or disorder suitable for treatment by gene therapy in the for future. Gene transfection methods of the invention comprise the steps of providing a positively chargeable biodegradable polymer composition comprising:

(a) at least one biologically active substance; and (b) A positively chargeable biodegradable polymer comprising at least one phosphoester linkage in the polymer backbone and at least one positively chargeable group wherein the positively chargeable group is a substituent of a side chain attached to the polymer backbone through a phosphoester linkage;

contacting the composition with a biological fluid, cell or tissue under conditions conducive to the delivery of at least a portion of the DNA sequence, gene or gene fragment to the biological fluid, cell or tissue.

DETAILED DESCRIPTION OF THE INVENTION

Figure 1:
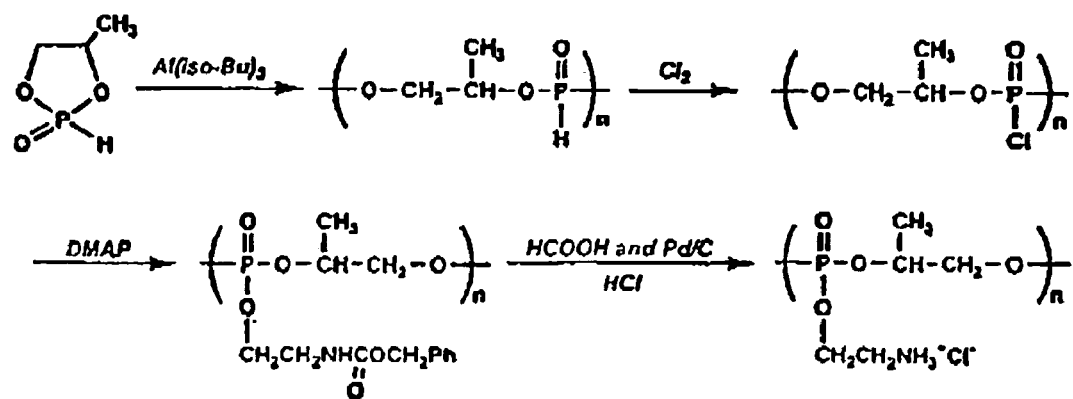
FIG. 1. Synthesis scheme of PPE-EA.

The biodegradable polyphosphoesters of the invention comprise the recurring monomeric units shown in the Formula I:

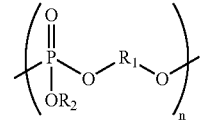

FORMULA I wherein:

$R_1$ is a divalent organic moiety that is aliphatic, aromatic or heterocyclic;

$R_2$ is alkyl, aryl, heteroaryl, heteroalicyclic, cycloalkyl, aralkyl, or cycloalkylalkyl; and each occurrence of $R_2$ is substituted with one or more positively chargeable functional groups (e.g. primary amino group, secondary amino group, tertiary amino group and quaternary amino group, etc.); and n is 5 to 2000.

Particularly preferred polymers according to formula I include polymers of formula II:

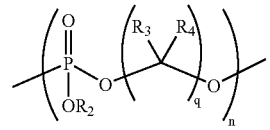

FORMULA II wherein:

$R_2$ is as defined in Formula I:

$R_3$ and $R_4$ are independently selected at each occurrence of $R_3$ and $R_4$ from the group consisting of hydrogen, alkyl, cycloalkyl, alkoxy, aryl, heteroaryl, heteroalicyclic, aralkyl, a steroid derivative; and q is an integer from about 1 to about 5.

Preferred positively chargeable biodegradable polymers of the invention are capable of forming a complex with negatively charged or neutral biologically active substances. Preferred biologically active substances include DNA, RNA, proteins, small molecule therapeutics, and the like.

Other preferred positively chargeable biodegradable polymers of the invention include polymers capable of complexing 20-60% by weight of a negatively charged or neutral biologically active substance such as DNA, RNA, proteins, small molecule therapeutics, and the like.

Furthermore, preferred positively chargeable biodegradable polymers of the invention include polymers having between about 5 and about 2,000 phosphate groups, more preferably between about 10 and about 1500 phosphate groups, and particularly preferred are polymers having between about 20 and 1000 phosphate groups. Also preferred are polymers having a molecular weight of between about 1000 and 500,000, more preferably having a molecular weight of between about 2000 and 200,000, particularly preferable are polymers having a molecular weight of between about 2000 and 100,000.

In additional preferred embodiments, positively chargeable biodegradable polymers of the invention further comprise one or more groups that facilitate intracellular or extracellular delivery of a negatively charged or neutral biologically active substance. Preferred groups for facilitating intracellular delivery of a biologically active substance include a lysosomalytic agent, an amphiphilic peptide, a steroid derivative, and the like.

In preferred embodiments, the biodegradable polyphosphoester polymers of the invention, including polymers according to Formula I or Formula II, are biocompatible before and upon degradation.

In another embodiment, the invention features a coacervate system useful for the delivery of bioactive macromolecules comprising the biodegradable polymer of Formula I.

In a further embodiment, the invention contemplates a process of making polymeric coacervates for delivery of bioactive macromolecules.

In yet another embodiment, the invention comprises articles comprising one or several different polymers with structures shown in Formula I and bioactive substances, e.g. nucleic acids and other negatively charged macromolecules for sustained release of these bioactive substances in-vivo and in-vitro. Additionally, the bioactive substances can be released in a controlled, sustained manner either an intracellular and extracellular manner. In a still further embodiment, the invention contemplates a process for preparing biodegradable polyphosphoesters, which comprises a step of reacting a polymer shown in Formula III, wherein X is a halogen and $R^1$ is as defined in Formula I, with an alcohol having a general structure as $R^2OH$, wherein $R_2$ is alkyl, aryl, heteroaryl, heteroalicyclic, cycloalkyl, aralkyl or cycloalkylalkyl wherein each occurrence of $R_2$ is substituted with one or more positively chargeable functional groups (e.g., primary amino group, secondary amino group, tertiary amino group and quaternary amino group, etc.).

FORMULA III

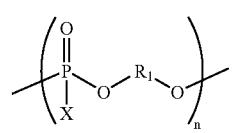

In specific embodiments, one or more charged groups present in $R_2$ are capable of reacting with a P-halogen bond.

Preferably, reactive charged groups are protected using standard organic chemistry protecting group techniques. The protected alcohol, $R_2OH$, is then reacted with the polymer of Formula III. In particularly preferred embodiments, reactive charged groups include primary or secondary amine groups.

The biodegradable polymeric system described in the present invention achieves sustained and localized delivery of one or more therapeutic agents to a designated biological tissue or site in a patient. In particular, the polymeric system of the invention achieves sustained and localized delivery of one or more genes in skeletal muscles or intradermally and achieve a higher gene transfer efficiencies than other plasmid delivery systems currently under investigation.

The polyphosphate carriers of the present invention typically offer the following advantages over other biodegradable carriers described in the literature and patents:

The polyphosphate carriers of the present invention are more efficient at binding to nucleic acids and proteins. In general, polymers provided herein have higher molecular weight than most other biodegradable carriers and a relatively high charge density, which leads to an increased binding capacity to plasmid DNA. Increased DNA binding capacity results in increased nucleic acid loading levels for the polyphosphate carriers provided herein. Compared to the PLGA microparticle systems reported in the literatures, the coacervate system provided by the present invention is capable of much higher loading levels of nucleic acids (in a range of 20 to 60%, as compared with less than 1% for the microparticle systems reported in the literatures). This is particularly beneficial when a higher dose of administration is needed.

The structures of the polyphosphate carriers of the present invention can be modified to have variable charge groups with different pKb, different charge density, molecular weight, hydrophilicity/hydrophobicity balance to optimize the degradation rate of the polymers, nucleic acid release rates from the systems and transfection activity of the polymers. Sustained release of plasmid DNA is achieved either in an extracellular or intracellular manner. For the intracellular delivery and sustained release of nucleic acids, a lysosomalytic agent, e.g. an amphiphilic peptide, could be conjugated to the carriers to enhance the lysosomal escape after cell uptake. A lipophilic moiety, e.g. a group bearing cholesterol structural or lipid, could be conjugated to the carriers to enhance the interaction between coacervates and cell membrane therefore facilitate cell uptake. A nucleus localization signal could be conjugated to the carriers to facilitate the nucleus translocation.

Polyphosphate polymers of the invention are biodegradable, such polymers have a cleavable backbone, which is cleaved by at least one pathway selected from hydrolystic or enzymatic degradation.

Polyphosphate polymers of the invention are biocompatible before, during and after biodegradation. Biodegradation breakdown products are typically non-toxic. The polyphosphoramidate polymers of the invention are less cytotoxic poly-L-lysine, PEI and liposome compositions in vitro. In one of the embodiment, polymer of Formula I degrades to phosphate, 1,2-propanediol and ethanolamine. The cytotoxicity assay suggests minimal toxicity when incubated with cells for 24 hours at a concentration higher than 500 µg/ml.

Polyphosphates suitable for use in the invention may be modified to comprise one or more specific ligands conjugated to the side chain or as a side chain group to enhance the cellular uptake or one or more bioactive molecules (nucleic acids and proteins) dispersed in carrier polymer and/or achieve tissue/cell specific delivery of the bioactive cargo.

Polyphosphates suitable for use in the methods of the present invention include any and all different single pure isomers and mixtures of two or more isomers. The term isomer is intended to include diastereoisomers, enantiomers, regioisomers, structural isomers, rotational isomers, tautomers, and the like. For compounds which contain one or more stereogenic centers, e.g., chiral compounds, the methods of the invention may be carried out with a enantiomerically enriched compound, a racemate, or a mixture of diastereomers. Preferred enantiomerically enriched compounds have an enantiomeric excess of 50% or more, more preferably the compound has an enantiomeric excess of 60%, 70%, 80%, 90%, 95%, 98%, or 99% or more.

Polyphosphates suitable for use in the methods of the present invention include any and all molecular weight distribution profiles, i.e., polymers having a $M_w$, or $M_n$ of between 1 and about 50, more typically a $M_w$, or $M_n$ between about 1.2 and about 10. Moreover, polyphosphroamidates of the invention have a polydispersity index of between about 1 and about 5.

As also discussed above, typical subjects for administration in accordance with the invention are mammals, such as primates, especially humans.

Biodegradable polymers differ from non-biodegradable polymers in that they can be degraded during in vivo therapy. This generally involves breaking down the polymer into its monomeric subunits. In principle, the ultimate hydrolytic breakdown products of polymers suitable for use in the methods of the present invention should be biocompatible, non-toxic and easily excreted from a patient's body. However, the intermediate oligomeric products of the hydrolysis may have different properties. Thus, toxicology of a biodegradable polymer intended for implantation or injection, even one synthesized from apparently innocuous monomeric structures, is typically determined after one or more toxicity analyses.

The biodegradable polymer of the invention is preferably sufficiently pure to be biocompatible itself and remains biocompatible upon biodegradation. "Biocompatible" is defined to mean that the biodegradation products and/or the polymer itself are nontoxic and result in only minimal tissue irritation when instilled in the bladder or transported or otherwise localized to other tissues within a patient.

It will be appreciated that the actual preferred amounts of therapeutic agent or other component used in a given composition will vary according to the therapeutic agent being utilized including the polymer system being employed, the mode of application, the particular site of administration, etc. Optimal administration rates for a given protocol of administration can be readily ascertained by those skilled in the art using conventional dosage determination tests conducted with regard to the foregoing guidelines.

As used herein, "alkyl" is intended to include branched, straight-chain and cyclic saturated aliphatic hydrocarbon groups including alkylene, having the specified number of carbon atoms. Examples of alkyl include, but are not limited to, methyl, ethyl, n-propyl, i-propyl, n-butyl, s-butyl, i-butyl, n-pentyl, and s-pentyl. Alkyl groups typically have 1 to about 16 carbon atoms, more typically 1 to about 20 or 1 to about 12 carbon atoms. Preferred alkyl groups are $C_1$-$C_{20}$ alkyl groups, more preferred are $C_{1-12}$-alkyl and $C_{1-6}$-alkyl groups. Especially preferred alkyl groups are methyl, ethyl, and propyl.

As used herein, "heteroalkyl" is intended to include branched, straight-chain and cyclic saturated aliphatic hydrocarbon groups including alkylene, having the specified number of carbon atoms and at least one heteroatom, e.g., N, O or S. Heteroalkyl groups will typically have between about 1 and about 20 carbon atoms and about 1 to about 8 heteroatoms, preferably about 1 to about 12 carbon atoms and about 1 to about 4 heteroatoms. Preferred heteroalkyl groups include the following groups. Preferred alkylthio groups include those groups having one or more thioether linkages and from 1 to about 12 carbon atoms, more preferably from 1 to about 8 carbon atoms, and still more preferably from 1 to about 6 carbon atoms. Alylthio groups having 1, 2, 3, of 4 carbon atoms are particularly preferred. Prefered alkylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkylsulfinyl groups having 1, 2, 3, or 4 carbon atoms are particularly preferred. Preferred alkylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alylsulfonyl groups having 1, 2, 3, or 4 carbon atoms are particularly preferred. Preferred aminoalkyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkyl groups having 1, 2, 3, or 4 carbon atoms are particularly preferred.

As used herein, "heteroalkenyl" is intended to include branched, straight-chain and cyclic saturated aliphatic hydrocarbon groups including alkenylene, having the specified number of carbon atoms and at least one heteroatom, e.g., N, O or S. Heteroalkenyl groups will typically have between about 1 and about 20 carbon atoms and about 1 to about 8 heteroatoms, preferably about 1 to about 12 carbon atoms and about 1 to about 4 heteroatoms. Preferred heteroalkenyl groups include the following groups. Preferred alkylthio groups include those groups having one or more thioether linkages and from 1 to about 12 carbon atoms, more preferably from 1 to about 8 carbon atoms, and still more preferably from 1 to about 6 carbon atoms. Alkenylthio groups having 1, 2, 3, or 4 carbon atoms are particularly preferred. Prefered alkenylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkenylsulfinyl groups having 1, 2, 3, or 4 carbon atoms are particularly preferred. Preferred alkenylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alkenylsulfonyl groups having 1, 2, 3, or 4 carbon atoms are particularly preferred. Preferred aminoalkenyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkenyl groups having 1, 2, 3, or 4 carbon atoms are particularly preferred.

As used herein, "heteroalkynyl" is intended to include branched, straight-chain and cyclic saturated aliphatic hydrocarbon groups including alkynylene, having the specified number of carbon atoms and at least one heteroatom, e.g., N, O or S. Heteroalkynyl groups will typically have between about 1 and about 20 carbon atoms and about 1 to about 8 heteroatoms, preferably about 1 to about 12 carbon atoms and about 1 to about 4 heteroatoms. Preferred heteroalkynyl groups include the following groups. Preferred alkynylthio groups include those groups having one or more thioether linkages and from 1 to about 12 carbon atoms, more preferably from 1 to about 8 carbon atoms, and still more preferably from 1 to about 6 carbon atoms. Alkynylthio groups having 1, 2, 3, or 4 carbon atoms are particularly preferred. Prefered alkynylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkynylsulfinyl groups having 1, 2, 3, or 4 carbon atoms are particularly preferred. Preferred alkynylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms, Alkynylsulfonyl groups having 1, 2, 3, or 4 carbon atoms are particularly preferred. Preferred aminoalkynyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkynyl groups having 1, 2, 3, or 4 carbon atoms are particularly preferred.

As used herein, "cycloalkyl" is intended to include saturated ring groups, having, the specified number of carbon atoms, such as cyclopropyl, cyclobutyl, cyclopentyl, or cyclohexyl. Cycloalkyl groups typically will have 3 to about 8 ring members.

In the term "($C_{3-6}$ cycloalkyl)$C_{1-4}$ alkyl", as defined above, the point of attachment is on the alkyl group. This term encompasses, but is not limited to, cyclopropylmethyl, cyclohexylmethyl, cyclohexylmethyl.

As used here, "alkenyl" is intended to include hydrocarbon chains of straight, cyclic or branched configuration, including alkenylene, and one or more unsaturated carbon-carbon bonds which may occur in any stable point along the chain, such as ethenyl and propenyl. Alkenyl groups typically will have 2 to about 12 carbon atoms, more typically 2 to about 12 carbon atoms.

As used herein, "alkynyl" is intended to include hydrocarbon chains of straight, cyclic or branched configuration, including alkynylene, and one or more triple carbon-carbon bonds which may occur in any stable point along the chain, such as ethynyl and propynyl. Alkynyl groups typically will have 2 to about 20 carbon atoms, more typically 2 to about 12 carbon atoms.

As used herein, "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1). Examples of haloalkyl include, but are not limited to, trifluoromethyl, trichloromethyl, pentafluoroethyl, and pentachloroethyl. Typical haloalkyl groups will have 1 to about 16 carbon atoms, more typically 1 to about 12 carbon atoms.

As used herein, "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups typically have 1 to about 16 carbon atoms, more typically 1 to about 12 carbon atoms.

"Prodrugs" are intended to include any covalently bonded carriers which release the active parent drug according to formula I in vivo when such prodrug is administered to a mammalian subject. Prodrugs of a compound are prepared by modifying functional groups present in the drug compound in such a way that the modifications are cleaved, either in routine manipulation or in vivo, to the parent compound.

Combinations of substituents and/or variables are permissible only if such combinations result in stable compounds. A stable compound or stable structure is meant to imply a compound that is sufficiently robust to survive isolation to a useful degree of purity from a reaction mixture, and formulation into an effective therapeutic agent.

As used herein, the term "aliphatic" refers to a linear, branched, cyclic alkane, alkene, or alkyne. Preferred aliphatic groups in the poly(phosphoester-co-amide) polymer of the invention are linear or branched and have from 1 to 20 carbon atoms.

As used herein, the term "aryl" refers to an unsaturated cyclic carbon compound with 4n+2 electrons where n is a non-negative integer, about 5-18 aromatic ring atoms and about 1 to about 3 aromatic rings.

As used herein, the term "heterocyclic" refers to a saturated or unsaturated ring compound having one or more atoms other than carbon in the ring, for example, nitrogen, oxygen or sulfur.

The polymers of the invention are usually characterized by a release rate of the therapeutic agent in vivo that is controlled at least in part as a function of hydrolysis of the phosphoester bond of the polymer during biodegradation. Additionally, the therapeutic agent to be released may be conjugated to the sidechain of the phosphramidate repeat unit to form a pendant drug delivery system. Further, other factors are also important.

The life of a biodegradable polymer in vivo also depends upon its molecular weight, crystallinity, biostability, and the degree of cross-linking. In general, the greater the molecular weight, the higher the degree of crystallinity, and the greater the biostability, the slower biodegradation will be.

The therapeutic agent of the invention can vary widely with the purpose for the composition. The agnet(s) may be described as a single entity or a combination of entities. The delivery system is designed to be used with therapeutic agents having high water-solubility as well as with those having low water-solubility to produce a delivery system that has controlled release rates. The terms "therapeutic agent" and "biologically active substance" include without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of useful therapeutic agents and biologically active substances include the following expanded therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, antiuricemic agents, anti-anginal agents, antihistamines, antitussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and antithyroid agents, uterine relaxants, vitamins, antigenic materials, and prodrugs.

Specific examples of useful therapeutic agents and biologically active substances, i.e., bioactive molecules, from the above categories include: (a) anti-neoplastics such as androgen inhibitors, antimetabolites, cytotoxic agents, immunomodulators; (b) anti-tussives such as dextromethorphan, dextromethorphan hydrobromide, noscapine, carbetapentane citrate, and chlophedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; (n) anti-infective agents such as anti-fungals, anti-virals, antiseptics and antibiotics; and (o) antigenic materials, partricularly those useful in vaccine applications.

Preferably, the therapeutic agent or biologically active substance is selected from the group consisting of DNA, polysaccharides, growth factors, hormones, anti-angiogenesis factors, interferons or cytokines, and pro-drugs. In a particularly preferred embodiment, the therapeutic agent is a DNA vaccine comprising a DNA sequence encoding an antigen, a DNA sequence encoding a cytokine or a mixture of DNA sequoces encoding an antigen and a cytokine.

Other preferred therapeutic agents are substances that are capable of modulating the immune response of a patient. Preferred therapeutic agents capable of modulating an immune response include protein vaccines or DNA vaccines. More preferred therapeutic agents capable of modulating an immune response are DNA vaccines. In general, DNA vaccine include vaccines which comprise a DNA sequence encoding an antigen, DNA sequence encoding a cytokine or a combination of DNA sequence encoding an antigen and DNA sequence encoding a cytokine.

Preferred cytokine additives suitable for use in a DNA vaccine include cytokines selected from interleukins or interferons which can shift a patient's immune response toward either a $T_H1$ or $T_H2$ response. Preferred cytokines suitable for use in modulating an immune response include interleukin-12, interleukin-10, interleukin-5, interleukin-4 and interferon-gamma. Other preferred cytokines include interferon for use in treatment of Hepatitis C.

Suitable genes for use in the methods of the invention encode therapeutic proteins for administration locally such as for use in treatment of muscle related diseases, such as the neuromuscular disorders and also for systemic delivery of therapeutic proteins such as secretory therapeutic proteins including, for example, interferon for use in treatment of Hepatitis C.

Methods of the present invention are suitable for any protein or DNA based vaccination method which induces either $T_H1$ $T_H2$ or a combination of $T_H1$ and $T_H2$ immunological responses. Methods are applicable for any illness or disease for which a vaccination is known or for which treatment is effected by systemic delivery of a therapeutic agent such as a small molecule drug, protein or DNA.

In preferred immune modulation methods of the invention, administration methods of the invention for delivering a therapeutic agent to the lymph nodes are suitable for delivering an therapeutic agent capable of modulating an immune response so that a patient's immune response is modulated. The lymph node is one of the primary sites for immune system stimulation; delivery of drugs, proteins, or DNA to these nodes results in the modulation of the immune response. After the microparticles are administered to the lymph nodes, they deliver their the therapeutic agent contained therein. Release of the therapeutic can be observed in by direct visualization of protein expression in cells of the lymph nodes, as well as indirect evidence through positive immune responses.

Other preferred therapeutic agents are substances that are capable of modulating the immune response of a patient. Preferred therapeutic agents capable of modulating an immune response include protein vaccines or DNA vaccines. More preferred therapeutic agents capable of modulating an immune response are DNA vaccines. In general, DNA vaccine include vaccines which comprise a DNA sequence encoding an antigen, DNA sequence encoding a cytokine or a combination of DNA sequence encoding an antigen and DNA sequence encoding a cytokine.

The therapeutic agents are used in amounts that are therapeutically effective. While the effective amount of a therapeutic agent will depend on the particular material being used, amounts of the therapeutic agent from about 1% to about 65% have been easily incorporated into the present delivery systems while achieving controlled release. Lesser amounts may be used to achieve efficacious levels of treatment for certain therapeutic agents.

In addition, the polymer composition of the invention can also comprise polymer blends of the polymer of the invention with other biocompatible polymers, so long as they do not interfere undesirably with the biodegradable characteristics of the composition. Blends of the polymer of the invention with such other polymers may offer even greater flexibility in designing the precise release profile desired for targeted drug delivery or the precise rate of biodegradability desired for structural implants such as for orthopedic applications. Examples of such additional biocompatible polymers include other polycarbonates; polyesters; polyorthoesters; polyamides; polyurethanes; poly(iminocarbonates); and polyanhydrides.

As a drug delivery device, the polymer compositions of the invention provide a polymeric matrix capable of sequestering a biologically active substance and provide predictable, controlled delivery of the substance. The polymeric matrix then degrades to non-toxic residues.

It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

A positively chargeable biodegradable polymer composition of the invention also may be packaged together with instructions (i.e. written, such as a written sheet) for treatment of a disorder as disclosed herein, e.g. instruction for treatment of a subject that is susceptible to or suffering from a disease or disorder which may be treated by administration of a bioactive molecule, e.g., therapeutic agent, dispersed in the positively chargeable biodegradable polymer composition.

A positively chargeable biodegradable polymer composition of the invention be administered parenterally, preferably in a sterile non-toxic, pyrogen-free medium. The drug, depending on the vehicle and concentration used, can either be suspended or dissolved in the vehicle. Advantageously, adjuvants such as local anesthetics, preservatives and buffering agents can be dissolved in the vehicle. The term parenteral as used herein includes injections and the like, such as subcutaneous, intradermal, intravascular (e.g., intravenous), intramuscular, intrasternal, spinal, intrathecal, and like injection or infusion techniques, with subcutaneous, intramuscular and intravascular injections or infusions being preferred.

A positively chargable biodegradable polymer composition of the invention also may be packaged together with instructions (i.e. written, such as a written sheet) for treatment of a disorder as disclosed herein, e.g. instruction for treatment of a subject that is susceptible to or suffering from inflammation, cellular injury disorders, or immune system disorders.

The present invention provides biocompatible and biodegradable gene carriers that release the DNA to a targeted tissue, cell or fluid in a sustained manner. In one embodiment, the invention provides a PPE-EA polyphosphate as a gene carrier. The structure of PPE-EA is built on a phosphate backbone with a 1,2-propylene diol moiety, and a charged aminoethyl side chain. The ultimate hydrolytic degradation products of this polymer are expected to be α-propylene glycol, phosphate and ethanolamine, all with minimal toxicity profiles. Such a design has led to a minimal toxicity profile of this polymer carrier, as demonstrated in the vigorous cytotoxicity assay, where gene carriers were incubated with cells for 24 hours. The acute tissue response to PPE-EA evaluated in mouse muscles also revealed a similar contrast, when compared with PEI at a same dose of positive charges.

PPE-EA has a relatively higher molecular weight compared with most other biodegradable gene carriers known in the art. The relatively high molecular weight of PPE-EA ($\overline{M}w$: 30,300, degree of polymerization: 100.2) was achieved by ring opening polymerization of a cyclic phosphate monomer. This feature coupled with the pedent chain charges has increased the ability of PPE-EA to form condensate complexes with DNA. Complete binding of DNA was achieved with PPE-EA at a charge ratio of 1, which was several folds lower than other biodegradable gene carriers. At this charge ratio, PPE-EA was shown to effectively protect plasmid DNA from DNase I degradation and serum degradation.

Applicants have also surprisingly discovered that the relatively high degradability of PPE-EA is suitable for the sustained release of DNA which occurs in connection with degradation of the polymeric phosphate carrier. DNA release occurred as early as a few hours at the low N/P ratios, to a few days of retardation for high N/P ratios. N/P ratio was the factor that dominated the kinetics of DNA release, especially in the first phase (within the first 6 days), during which period the DNA release rate decreased with the increase of N/P ratio. Such an adjustable DNA release kinetics is potentially advantageous in achieving different intracellular and extracellular sustained release of DNA. Nevertheless, the DNA release rate should be optimized for each particular application.

The PPE-EA/DNA complexes of the invention offer superior controlled release profiles when compared with the biodegradable polymer based systems described in the literature, e.g. PLGA and polyanhydride micro/nanoparticles. Loading levels of DNA achieved in this system were much higher than that in PLGA microparticles. For example, PPE-EA/DNA complexes with a N/P ratio of 1 have a DNA payload of 60%, comparing with less than 2% for PLGA or polyanhydride microspheres. Higher loading level reduced the use of carriers significantly. Moreover, the PPE-EA/DNA system was prepared by complex coacervation versus the double emulsion method for the microsphere systems. The former involved only aqueous conditions at room temperature, whereas the latter involved organic solvent and sonication/vortexing. The mild preparation conditions yielded good structural and functional integrity of the DNA released from PPE-EA/DNA complexes.

The sustained gene delivery system provided by the present invention is suitable for use in administration of gene delivery intramuscularly. This has to be compared to naked DNA injection, which is somewhat effective in affording both local and systemic transgene expression. Intramuscular administration of PPE-EA/DNA complexes resulted in significantly higher and delayed β-gal expression in muscle, although the enhancement effect becomes less prominent at higher administration dose. The higher β-gal level in the PPE-EA mediated gene transfer is presumably due to the sustained release of plasmid at the injection site and the protection of plasmid by PPE-EA. Compositions of a positively chargeable phosphate polymer and DNA provided by the present invention which have a lower N/P ratio (<1) achieved higher levels of gene expression, suggesting the complicated mechanism in gene delivery to skeletal muscle. Compositions having higher N/P ratios such as 1.5 or 2 gave background level of gene expression in the muscle. This diminished gene expression was not likely due to any toxicity of PPE-EA in the complexes at higher N/P ratio, since the total amount of PPE-EA used in this formulation was only 20% of the dose tested for the tissue compatibility experiment. Muscle biopsy in these groups did not show any noticeable toxicity either. This is also consistent with the results from other cationic polymer/DNA complexes in muscle injection formulation, where no positive gene transfection has been reported. A recent study revealed that intramuscular injection of PEI/DNA complexes induces gene expression in central nervous system (e.g. brain stem) through retrograde transport of the complexes/particles (13). It is unclear yet if these PPE-EA/DNA complexes were transported out of the muscle in a similar manner.

This enhancement of gene expression may be applied to deliver therapeutic proteins to systemic circulation such as the delivery of IFN-α2b. This is a secretory protein that has a serum half-life of 1.7 hours (14). An N/P ratio of 0.5 has been selected due to its higher efficiency in the previous study. Following intramuscular injection, PPE-EA/DNA complexes generated 1.8 times higher IFN-α2b in blood circulation than naked DNA on day 14 (p<0.05), although at other time points, the expression levels were similar to that of naked DNA injection. This is particularly significant because of the short half-life of IFN-α2b. It is worth noting that this result was obtained at a relatively higher dose of DNA (50 μg). As suggested by the β-gal experiment, the enhancement effect by PPE-EA/DNA complexes might be more significant at lower doses.

The positively chargeable biodegradable polyphosphates provided by the present invention are the first polymeric carriers capable of inducing higher levels of gene expression in muscle than naked DNA. Although the experimental protocol was far from optimized, these results suggested the potential of PPE-EA as a gene carrier for the local delivery as well as systemic delivery of protein pharmaceutics.

In one embodiment, the present invention provides a novel controlled gene delivery system based on a water soluble and biodegradable polyphosphoester, poly(2-aminoethyl propylene phosphate) [PPE-EA]. The polymer degraded in PBS at 37° C. through the cleavage of the backbone phosphate bonds, and it was synthesized with a relative high molecular weight to ensure a suitable hydrolytic stability as a gene carrier. The tissue response and cytotoxicity study demonstrated a better tissue compatibility of PPE-EA in mouse muscle compared to commonly used polyethylenimine and poly-L-lysine. PPE-EA condensed DNA efficiently and protected DNA from nuclease and serum degradation. Sustained release of plasmid was achieved from PPE-EA/DNA complexes as a result of PPE-EA degradation. The DNA release profiles appear to be predominantly controlled by carrier degradation and the release rate of plasmid could be adjusted by varying the charge ratio of PPE-EA to DNA. At an N/P (amino to phosphate groups) ratio of 1, a 46% burst was observed for the first day, followed by about 4% release per day (24 μg DNA/day/mg of complex) for 12 days. Higher charge ratios reduced both the DNA release rate and the burst effect. The released DNA retained its structural and functional integrity. Intramuscular injection of PPE-EA-p43-LacZ complexes at N/P ratios of 0.5 and 1 resulted in enhanced β-galactosidase expression in anterior Tibialis muscle in Balb/c mice, as compared with naked DNA injections. Similarly, PPE-EA/IFNα2b DNA complexes generated an increased systemic level of interferon-α2b in mouse serum following intramuscular injection, as compared with naked DNA injection.

The following examples are illustrative of the invention. All documents mentioned herein are incorporated herein by reference.

EXAMPLES

The following examples are offered by way of illustration and are not intended to limit the invention in any manner.

Example 1

Synthesis and Characterization of Polyphosphoramidates

The synthetic scheme is shown in FIG. 1.

1.1 Synthesis of poly(4-methyl-2-oxo-2-hydro-1,3,2-dioxaphospholane)

1.2

4-methyl-2-oxo-2-hydro-1,3,2-dioxaphospholane (58 g, 0.475 mol) [freshly prepared according to Lucas' method (Lucas, Mitchell, and Scully, 1950, *Cyclic phosphites of some aliphatic glycols. J. Am. Chem. Soc.* 72: 5491-5497) was polymerized in 200 ml of fresh dried $CHCl_3$ at room temperature for 48 hours. Polymerization was initiated with triisobutylaluminum (1 wt %, 4 ml of 15% solution in heptane). The polymer was obtained by precipitation into anhydrous benzene. This polymer became insoluble in chloroform after precipitation, but it is soluble in anhydrous DMF.

1.2 Synthesis of poly(4-methyl-2-oxo-2-chloro-1,3,2-dioxaphospholane)

40 mL of polymer solution from the former step was added into 200 ml of dried benzene. The precipitate was dried under vacuum and weighted to obtain white polymer (4.187 g). This polymer was then suspended in dried $CH_2Cl_2$ and dry $Cl_2$ was passed. The suspension was dissolved during chlorination. Addition of $Cl_2$ was stopped at the first appearance of a persistent yellow color. The excess of $Cl_2$ was removed under vacuum until a colorless solution resulted. This solution was further used for preparation of different derivatives without polymer isolation.

1.3 Synthesis of Poly(4-methyl-2-oxo-2-(N-benzyloxycarbonyl)-aminoethyloxy-1,3,2-dioxaphospholane)

To the cooled solution of poly(4-methyl-2-oxo-2-chloro-1,3,2-dioxaphospholane) (24.4 mmol of P—Cl) in $CH_2Cl_2$ from the former step, was added DMAP (6.56 g, 53.6 mmol), then the solution of benzyl N-(2-hydroxyethyl) carbamate (5.24 g, 26.9 mmol) was added dropwise from an addition funnel. After the addition, the mixture was heated and the mixture was allowed to reflux for 48 hours. The solution was washed with 1N HCl twice and water twice. The organic layer was dried over anhydrous magnesium sulfate and concentrated. The product was obtained by pouring the concentrated solution into ether as a white glassy solid (4.6 g, yield 60%).

1.4 Synthesis of poly(4-methyl-2-oxo-2-aminoethyloxy-1,3, 2-dioxaphospholane)

Figure 2:
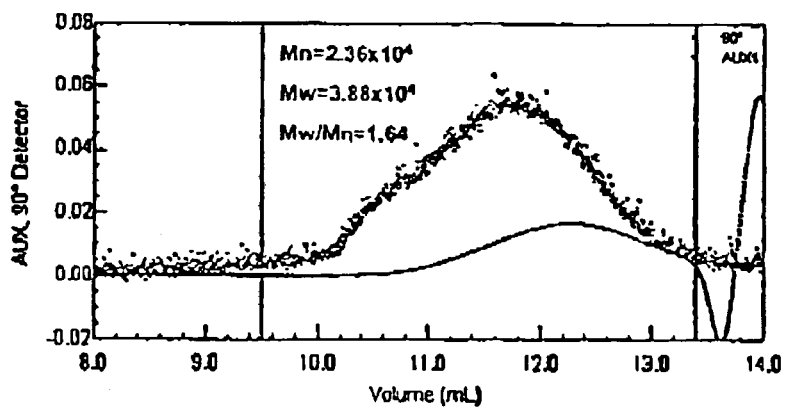
FIG. 2. Gel permeation chromatograph of PPE-EA.

Remove of the Cbz group was accomplished using formic acid and Pd/C according to a reported method (Zhou and Kohn, 1990, *Preparation of poly(L-serine ester): A Structural analogue of conventional poly(L-serine)*, Macromolecules 23: 3399-3406). In a 25 ml round-bottom flask the polymer (300 mg) was dissolved in 4 ml of DMF. To this solution under a $N_2$ atmosphere was added 1 g of Pd/C (10%, Aldrich). With vigorous stirring formic acid (14 ml) was added dropwise over 15 min. The reaction was stirred at room temperature for 14 hours and filtered to remove Pd/C. The catalyst was washed with 20 ml of 1N HCl. The filtrates were combined and concentrated under vacuum using a water bath below 45° C. to a volume of 5 ml whereupon 10 ml of 1N HCl was added. The solution was reconcentrated as above to a volume of 1 ml and then added dropwise to 150 ml of acetone with stirring and cooled to −20° C. The polymer was isolated and dried thoroughly under vacuum. Yield 166 mg (80%). The structure of PPE-EA was confirmed by NMR. The weight average molecular weight of PPE was 38,800 with a polydispersity index of 1.64 as determined by GPC/LS/RI method (FIG. 2).

Example 2

Assay for the Cytotoxicity of PPE-EA

Cytotoxicity of PPE-EA in comparison with other potential gene carriers [poly-L-lysine (PLL) and polyethylenimine (PEI)] is evaluated using the MTT assay. COS-7 cells (6,000 per well) were seeded in 96-well plates and incubated for 24 hours at 37° C. in 5% $CO_2$ followed by adding polymer solutions (50 µl) at different concentrations (0-1 mg/ml). After 24 hours incubation, cell viability was analyzed by a MTT assay according to Hansen's method (Hansen, et al., 1989, *J. Immunol. Methods*, 119: 203-210).

Figure 3:
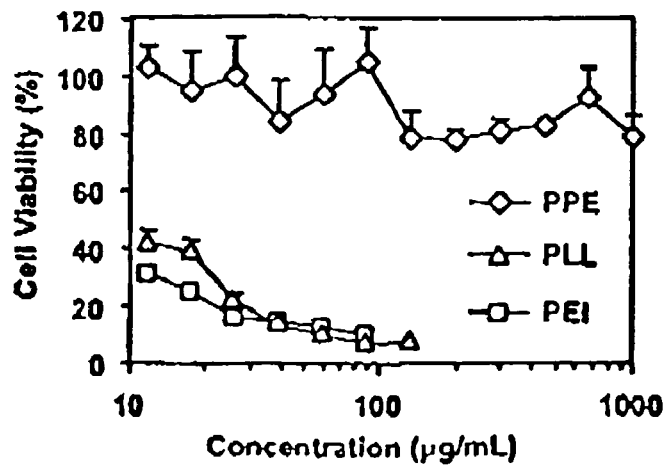
FIG. 3. Cytotoxicity of PPE-EA in COS-7 Cells as compared with PEI and PLL.

The assay results showed no significant change in morphology and proliferation rate as compared with cells without treatment, when PPE-EA was incubated with cells for 24 hours at a dose up to 0.5 mg/ml. In contrast, $LD_{50}$ values of PEI and PLL in this assay were below 10 µg/ml (FIG. 3). Similar results were observed in HEK 293 cells. This suggested that PPE-EA have a minimal cytotoxicity.

Example 3

Gel Retardation Assay for the DNA Binding Capacity of PPE-EA

Figure 4:
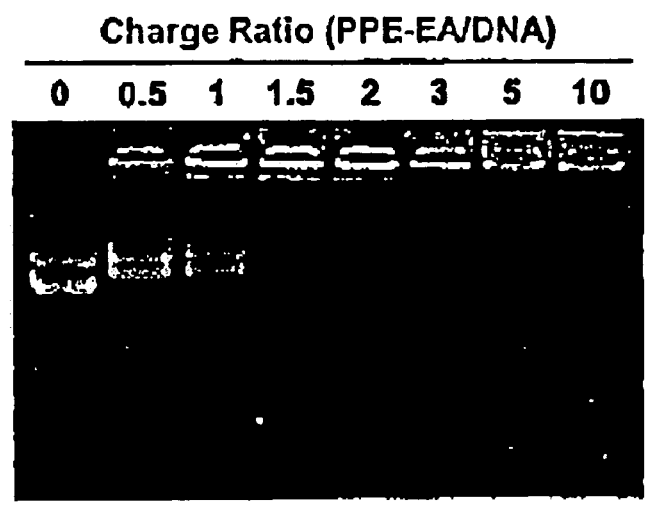
FIG. 4. Gel electrophoretic analysis of the complexation of PPE-EA with DNA.

To 2 µg or plasmid DNA dissolved in 20 µl of saline was added a PPE-EA solution in 20 µl of saline at the increasing charge ratios from 0.5 to 10 respectively. The mixture was vortexed for 20 seconds and the coacervates were incubated at room temperature for 30 minutes and then 10 µl of coacervates was analyzed on a 0.8% agrose gel. Formation of coacervates between plasmid DNA and PPE-EA was confirmed by gel retardation assay (FIG. 4). Complete binding of plasmid DNA was achieved at a charge ratio (N/P ratio) of 1 and above. PPE-DNA coacervates at charge ratio of 1 and above provided partial protection to plasmid DNA from nuclease degradation.

Example 4

Preparation of Coacervates and Release of Plasmid DNA From PPE-DNA Coacervates

PPE-EA-DNA coacervates were prepared in PBS with 1 mM EDTA by mixing plasmid DNA (60 µg/ml) with PPE-EA solution with concentration ranging from 20 µg/ml to 80 µg/ml to achieve various charge ratios (0.5 to 2). The coacervates were incubated at room temperature for 30 minutes before use. Plasmid DNA release from the coacervates was performed at 37° C. At various time points, samples were centrifuged and DNA concentration in the supernatant was measured by UV spectrophotometry at 260 nm. The integrity of DNA released form the coacervates was analyzed by gel electrophoresis (0.8% agrose gel).

Figure 5:
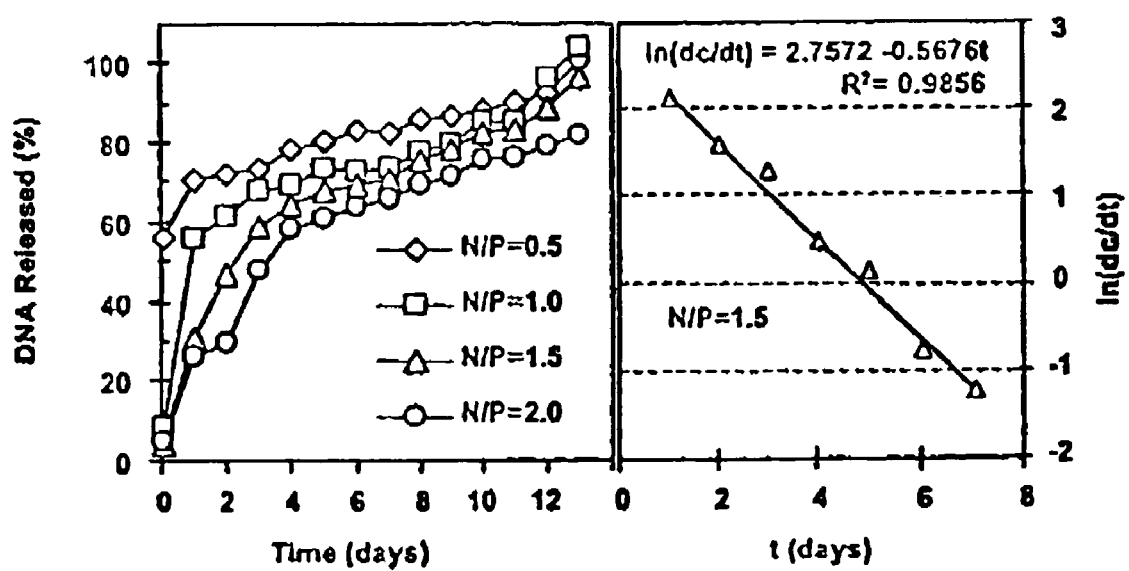
FIG. 5. In vitro release profiles of plasmid DNA from PPE-EA-DNA coacervates prepared at different charge ratios.

Plasmid DNA released from PPE-EA-DNA coacervates over a period of two weeks when the coacervates were incubated in PBS. A sustained release profile for up to two weeks from the coacervates was observed as a result of degradation of PPE. The release rate was a function of charge ratio (FIG. 5). When the coacervates were prepared at a N/P ratio of 1, a burst of 14.1 µg/ml was observed for the first day, then followed by a near constant release of 1.24 µg/ml/day for 12 days. At a N/P ratio of 1.5, DNA release followed first order release for the first week and then was near constant for the next week at a rate of 1.1 µg/ml/day. Whereas at a charge ratio of 2, DNA released at a slower rate, with an average of 3.2 µg/ml/day for the first 4 days and then 0.8 µg/ml/day for the next nine days. No burst effect was observed for N/P ratios of 1.5 and above. DNA release from these PPE-EA-DNA coacervates remained intact as indicated by the gel electrophoretic analysis, although some nicking of plasmid occurred during the incubation.

Example 5

Transfection Efficiency of PPE-EA-DNA Complex in HEK293 Cells

In vitro transfection of HEK293 cells with PPE-EA-DNA coacervates was evaluated using luciferase as a marker gene. Cells were seeded 24 hours prior to transfection into a 24-well plate (Becton-Dickinson, Lincoln Park, N.J.) at a density of $8 \times 10^4$ per well with 1 ml of complete medium (DMEM containing 10% FBS, supplemented with 2 mM L-glutamate, 50 units/ml penicillin and 50 µg/ml streptomycin). At the time of transfection, the medium in each well was replaced with 1 ml of serum free DMEM. PPE-EA-DNA coacervates or PEI-DNA complexes or PLL-DNA complexes were incubated with the cells for 3 hours at 37° C. The medium was replaced with 1 ml of fresh complete medium and cells were further incubated for 48 hours. All the transfection tests were performed in triplicate. After the incubation, cells were permeabilized with 200 µl of cell lysis buffer (Promega Co., Madison, Wis.). The luciferase activity in cell extracts was measured using a luciferase assay kit (Promega Co., Madison, Wis.) on a luminometer (Lumat9605, EG&G Wallac). The light units (LU) were normalized against protein concentration in the cell extracts, which was measured using BCA protein assay kit (Pierce, Rockford, Ill.).

Figure 6:
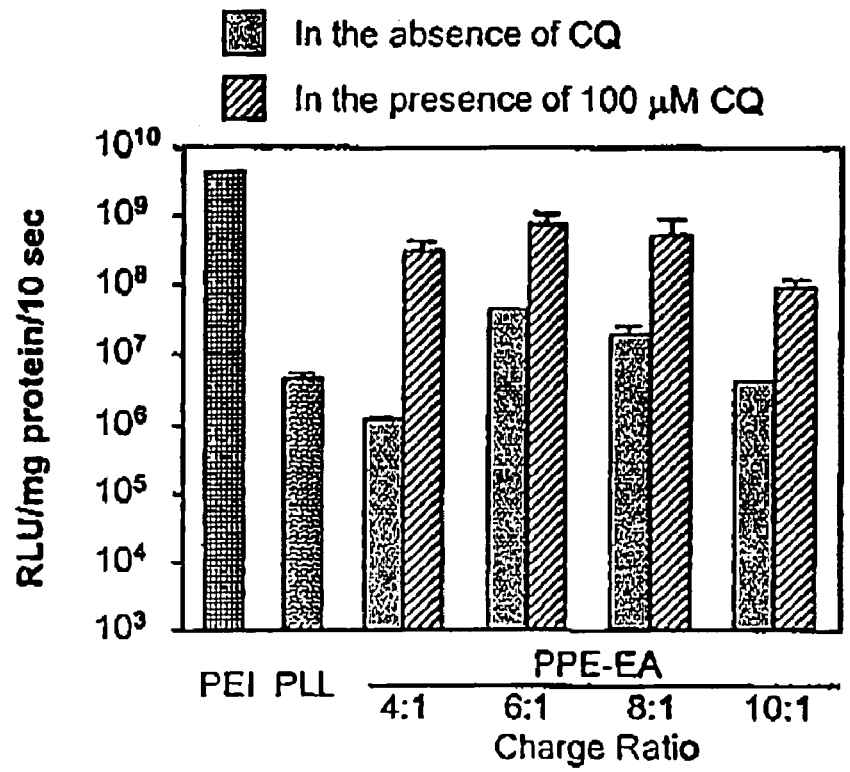
FIG. 6. In vitro transfection efficiency of PPE-EA-DNA coacervates in HEK 293 cells.

FIG. 6 showed the transfection efficiency of PPE-EA-DNA coacervates prepared at different charge ratios. As the gel electrophoresis analysis showed, at a +/− charge ratio of 1.0 and above, all the plasmid DNA added to the preparation mixture complexed with PPE-EA. However, coacervates with a charge ratio lower than 4 failed to show significant gene expression level. The highest level of gene transfection was observed with the coacervates synthesized at +/− charge ratios between 6 and 8.

The transfection ability of PPE-EA-DNA coacervates suggested that the controlled release feature of this gene delivery technology could also beneficial in an intracellular gene delivery application.

Chloroquine was shown to enhance the transfection efficiency of PPE-EA-DNA coacervates in vitro. FIG. 6 also included the transfection efficiency of PPE-EA-DNA coacervates with 100 µg/ml of CQ as a comparison. It was evident that CQ can enhance the transfection efficiency for about 10 to 100 times at this concentration. The enhancement effect was more prominent for the coacervates prepared at lower charge ratio, suggesting the competition between the endosomal escape and DNA release and degradation inside the cells.

Example 6

β-Galactosidase Expression in Mouse Muscle Following Intramuscular Injection

Balb/c mice (three per group) received bilateral injections in the anterior tibialis muscle of 2 µg of p43-LacZ, or PPE-p43-LacZ coacervates prepared in saline at different charge ratios (0.5 and 1.0). The injected muscles were isolated on day 1, 3, 7 and 14. The expression level of β-galactosidase in the muscle was measured using a β-Gal Reporter Gene Assay kit (Roche Molecular Biochemicals) using β-galactosidase as a standard.

Figure 7:
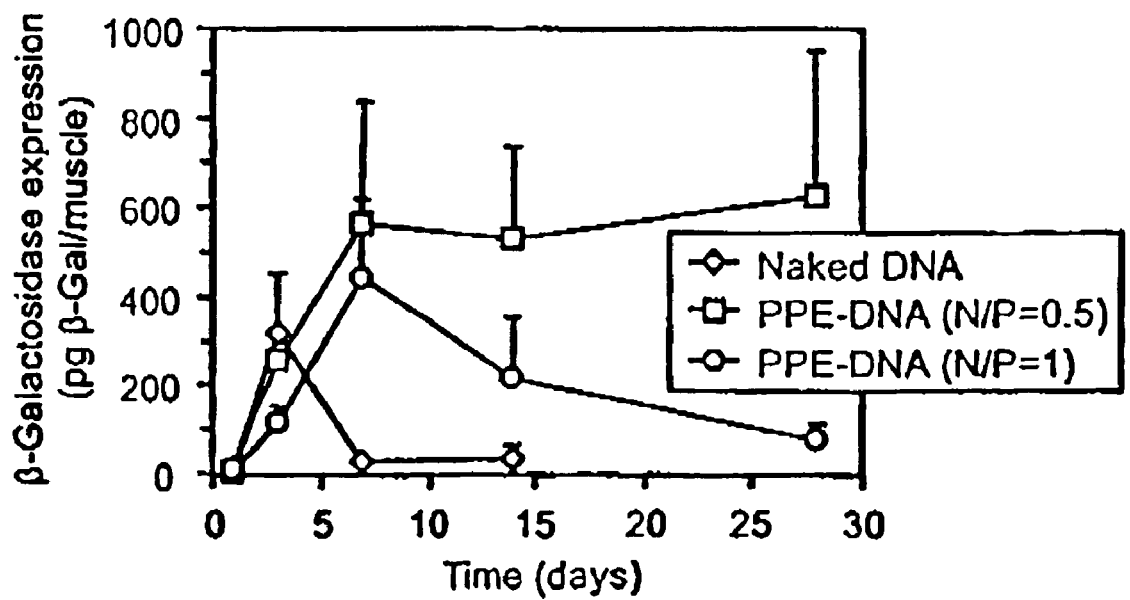
FIG. 7. Beta-galactosidase level in mouse muscle following intramucular injection of PPE-EA-DNA coacervates at a dose of 2 μg DNA/muscle.

Intramuscular injection of PPE-p43-LacZ complexes at an N/P ratio of 0.5 resulted in a sustained level of β-galactosidase expression in anterior tibialis muscle in Balb/c mice. At a dose of 2 µg of DNA per muscle, PPE-DNA complexes with an N/P ratio of 0.5 yielded a 20-fold higher β-Gal expression on day 7 than naked DNA group and the gene expression level persisted for upto 4 weeks (FIG. 7). Interestingly, complexes with an N/P ratio of 1, although had a delayed gene expression than naked DNA injection, yielded a lower level of β-Gal expression than complexes at N/P ratio of 0.5. A different set of experiment with a dose of 10 µg of DNA injection showed the similar trend.

Example 7

Tissue Response of PPE-EA in Mouse Muscle

PPE-EA or PEI dissolved in saline (40 µl) was injected into the tibialis anterior muscle in Balb/c mice at a dose equivalent to 60 nmol of positive charge (13.1 µg/40 µl for PPE-EA and 2.5 µg/40 µl for PEI). The muscles received the polymer injections were isolated at days 7, fixed in phosphate buffered formalin (10%), washed, and embedded in paraffin. Tissue sections were cut with 8 µm in thickness, placed on gelatin coated slides, and stained with hematoxylin and eosin (H&E) for histological examination. The tissue response was evaluated by an independent pathologist. Mice receiving intramuscular injection of 40 µl of saline were used as a control for this experiment.

Six to eight-week-old female Balb/c mice were obtained and housed in National University of Singapore Animal Holding Unit. Mice were maintained on ad libitum rodent feed and water at room temperature, 40% humidity. All animal procedures were approved by the National University of Singapore Faculty of Medicine Animal Care and Use Committee.

Figure 8:
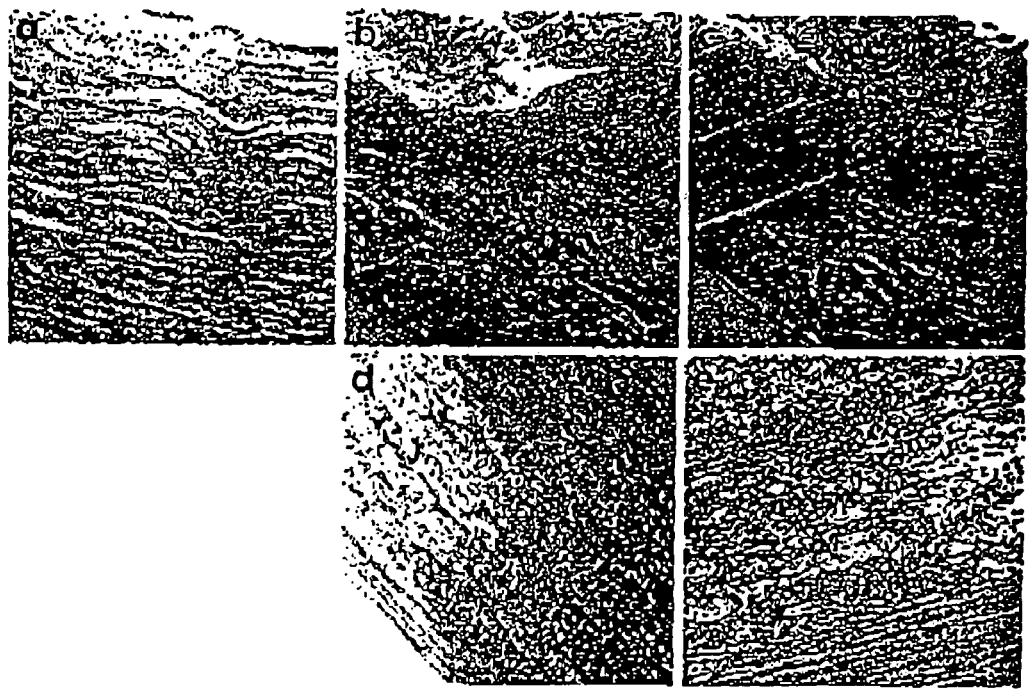
FIG. 8. Tissue response at day 7 following intramuscular injection of PPE-EA and PEI. (a) Saline injection (40 μl), showed normal tissue; (b) & (c): PPE-EA injection (13.1 μg, 60 nmole amino group), showed focal inflammation; (d) & (e): PEI (Mw 25 KDa, 2.5 μg, 60 nmole charged groups), showed severe inflammation and muscle necrosis.

The acute tissue response to PPE-EA was evaluated in muscles in Balb/c mice, using saline and PEI injections as controls. PPE-EA and PEI were given at the same dose of positive charge (60 nmol of amino groups for PPE-EA and 60 nmol of total amino groups for PEI), to allow for a fair comparison with the assumption that the toxicity of these polymers predominantly stems from their cationicity. As a result, PPE-EA was given at a higher amount, 5.2 folds higher than PEI in mass (13.1 µg of PPE-EA versus 2.5 µg of PEI per injection). Histological analysis at day 7 revealed mild inflammatory reaction at muscle sites injected with the PPE-EA (FIG. 8), whereas severe inflammatory response was observed in the PEI group. Moreover, severe necrosis was noticeable in all the muscle samples receiving PEI injection, with a large amount of macrophages, histiocytes and neutrophils present at the injection sites.

Example 8

Delivery of Interferon-α2b to Systemic Circulation Using PPE-EA/DNA Complexes

A plasmid, pCMV-IVS-IFN-mod2, encoding interferon-α2b (IFN-α2b) was used to test the effectiveness of PPE-EA as a carrier for the systemic delivery of secretory proteins via intramuscular injection. It was provided by The Immune Response Corporation (Carlsbad, Calif.) as a gift.

pCMV-IVS-IFN-mod2 plasmid DNA was dissolved in saline at a concentration of 1.25 mg/ml. Complexes were prepared by adding 40 µl of PPE-EA solution (0.41 mg/ml in saline) to 40 µl of DNA solution containing 50 µg DNA to achieve the N/P ratio of 0.5 and vortexed for about 20 seconds. The complexes were incubated at room temperature for 60 minutes. Balb/c mice (6 to 8 weeks old, five to seven mice per group) received bilateral injections in the tibialis anterior muscle of 40 µl of complexes containing 25 µg of DNA. One group of mice received bilateral injections of 25 µg of plasmid DNA in 40 µl of saline, and another group of mice receiving 40 µl of saline was used as the background control. The mice were bled at days 6, 10, 14 and 21, and serum samples were isolated and stored at −80° C. until assay. The concentrations of interferon-α2b in serum at different time points were analyzed using a human IFN-α ELISA kit (Pierce Endogen, Inc. Woburn, Mass.).

Figure 9:
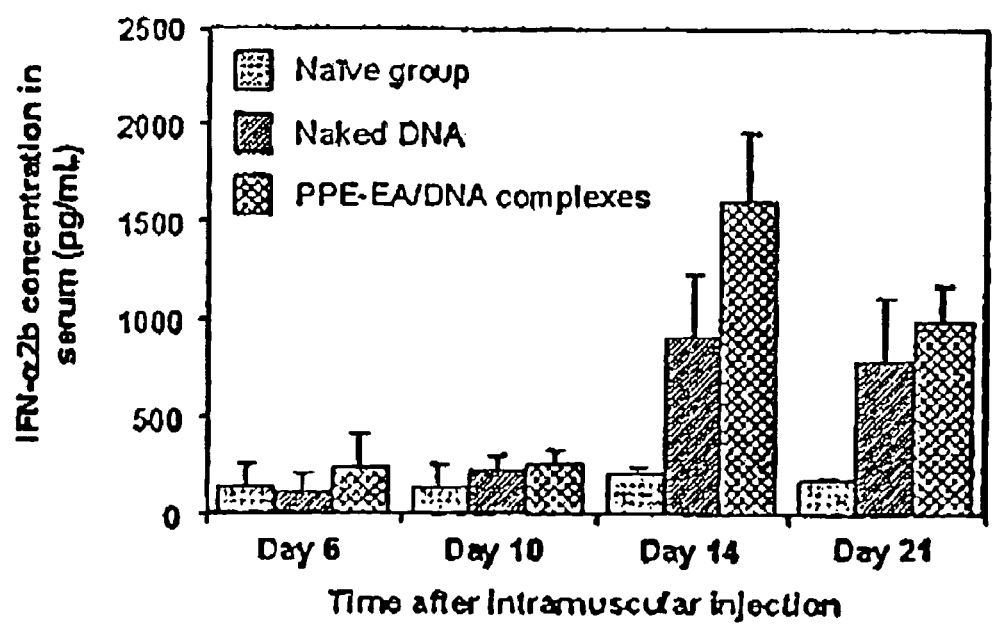
FIG. 9. IFN-α2b concentration in serum of mice following intramuscular injection of naked DNA (n=5~7) or complexes at N/P ratio of 0.5 (n=5~7). Each mouse received a dose equivalent to 50 μg of plasmid DNA. Naïve mice served as a control (n=4).

No significant level of IFN-α2b was detected in mice received 50 µg of naked DNA injection until day 14, reaching 917 pg/ml and 790 pg/ml of IFN-α2b in serum on day 14 and 21, respectively. Comparing with naked DNA injection, PPE-EA mediated gene transfer yielded a higher serum IFN-α2b of 1.61 ng/ml on day 14 (p<0.05), although IFN-α2b concentration in serum declined to similar level as naked DNA on day 21 (FIG. 9).

What is claimed is:

1. A water soluble and positively charged biodegradable polymer that is capable of forming a complex with negatively charged biologically active substances in aqueous solutions and comprises the recurring monomeric unit shown in Formula I:

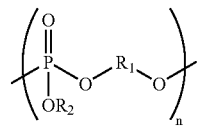

FORMULA I wherein
$R_1$ is a divalent aliphatic organic moiety;
$R_2$ is a positively charged alkyl or heteroalicyclic group selected from the groups consisting of primary amine, secondary amine, teriary amine, and quaternary amine;
m is an integer from 1 to 6;
n is from 20 to 2,000.

2. A water soluble and positively charged biodegradable polymer of claim 1, wherein the biodegradable polymer has between about 30 and about 200 phosphate groups in the backbone.

3. A water soluble and positively charged biodegradable polyphosphate of claim 1, wherein $R_1$ is defined in Formula II,

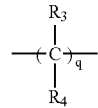

FORMULA II

Wherein
Each occurrence of $R_3$ and $R_4$ are independently selected from the group consisting of hydrogen or alkyl group; and
q is 2 to 4.

4. A method of preparing a water soluble and positively chargeable biodegradable polymer of Formula I, comprising the steps of:
(a) reacting a precursor polymer with recurring unit shown in Formula III,

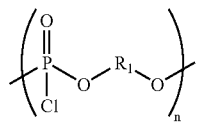

FORMULA III wherein
R$_1$ is a divalent aliphatic organic moiety;
with an alcohol having a structure of HO(CH$_2$)$_m$R$_2$, wherein R$_2$ is a positively charged alkyl or hertoalicyclic group selected from the groups consisting of protected primary amine, protected secondary amine, tertiary amine, and quaternary amine and m is an integer from 1 to 6; followed by (b) deprotecting the protected charge groups, if applicable.

5. A method of preparing a water soluble and positively charged biodegradable polymer as described in claim 4, wherein the biodegradable polymer has between 30 and 200 phosphate groups.

* * * * *

UNITED STATES PATENT AND TRADEMARK OFFICE
CERTIFICATE OF CORRECTION

PATENT NO.         : 7,345,138 B2
APPLICATION NO.    : 10/499898
DATED              : June 16, 2005
INVENTOR(S)        : Jun Wang, Hai-Quan Mao and Weng Leong It is certified that error appears in the above-identified patent and that said Letters Patent is hereby corrected as shown below:

Col 20, claim 1

Lines (27-33) (Formula I):

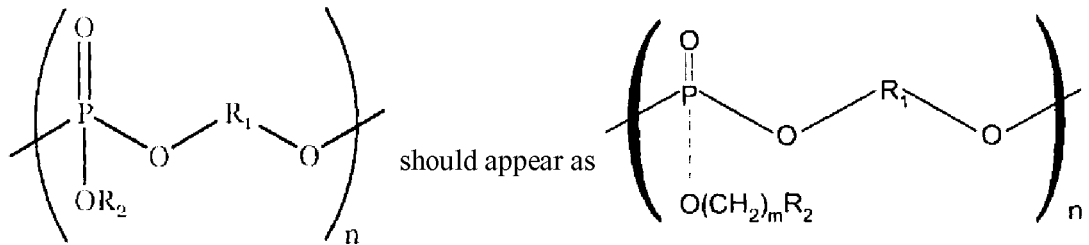

Signed and Sealed this

Twentieth Day of January, 2009

JON W. DUDAS
*Director of the United States Patent and Trademark Office*

UNITED STATES PATENT AND TRADEMARK OFFICE
CERTIFICATE OF CORRECTION

PATENT NO. : 7,345,138 B2  
APPLICATION NO. : 10/499898  
DATED : March 18, 2008  
INVENTOR(S) : Jun Wang, Hai-Quan Mao and Weng Leong Page 1 of 1

It is certified that error appears in the above-identified patent and that said Letters Patent is hereby corrected as shown below:

Col 20, claim 1

Lines (27-33) (Formula I):

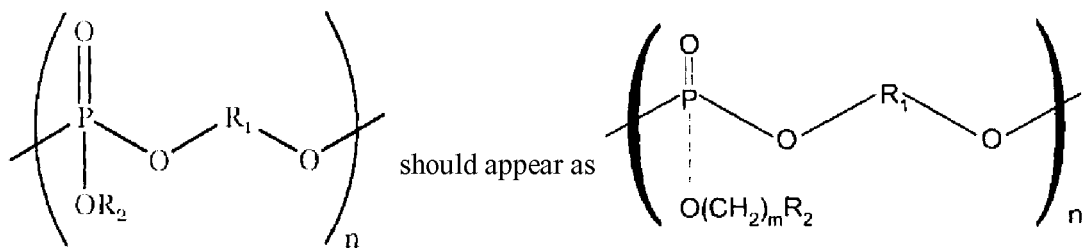

This certificate supersedes the Certificate of Correction issued January 20, 2009.

Signed and Sealed this

Seventeenth Day of February, 2009

JOHN DOLL  
*Acting Director of the United States Patent and Trademark Office*